(12) United States Patent
van Veen et al.

(10) Patent No.: US 9,664,662 B2
(45) Date of Patent: May 30, 2017

(54) MEANS AND METHODS FOR CLASSIFYING EGGS AS ORGANIC

(71) Applicant: Nederlandse Organisatie voor toegepast-natuurwetenschappelijk onderzoek TNO, Delft (NL)

(72) Inventors: Jacobus Johannes Frederik van Veen, Delft (NL); Ivana Bobeldijk-Pastorova, Delft (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 0 days.

(21) Appl. No.: 14/154,420

(22) Filed: Jan. 14, 2014

(65) Prior Publication Data
US 2014/0199701 A1    Jul. 17, 2014

(30) Foreign Application Priority Data

Jan. 17, 2013    (EP) ..................................... 13151701

(51) Int. Cl.
    *C07C 35/16*       (2006.01)
    *G01N 33/08*       (2006.01)

(52) U.S. Cl.
    CPC ..................................... *G01N 33/08* (2013.01)

(58) Field of Classification Search
    CPC ................................ C07C 35/16; G01N 33/08
    USPC .............................................. 568/833; 435/4
    See application file for complete search history.

(56) References Cited

U.S. PATENT DOCUMENTS 5,696,325 A     12/1997    Coucke et al.

FOREIGN PATENT DOCUMENTS

WO       02/083848 A2    10/2002
WO       2010/125345 A1   11/2010

OTHER PUBLICATIONS

Drew et al. Application of Vapor Phase Chromatography to Mass Spectrometer Analysis; Analytical Chemistry, vol. 28, No. 6 (1956) pp. 979-983.*
Clements et al. Myo-Inositol Content of Common Foods: Development of a High-Myo-Inositol Diet; The American Journal of Clinical Nutrition, vol. 33 (1980) pp. 1954-1967.*
Martin et al. Lab-on-a-Chip GC for Environmental Research; LCGC Europe, vol. 23, No. 10 (2010) downloaded from www.chromatographyonline.com/lab-chip-gc-environmental-research on Jun. 25, 2015.*
European Search Report, EP 13 15 01701, search completed Sep. 18, 2013 (2 pages).

* cited by examiner

*Primary Examiner* — Scott Long
*Assistant Examiner* — Paul Martin
(74) *Attorney, Agent, or Firm* — Thompson Hine LLP (57) ABSTRACT

Methods are provided for determining whether a chicken egg, or a chicken egg pool, belongs to a class of organic chicken eggs. The yolk scyllo-inositol and myo-inositol concentrations, or concentration-related signals or values, are measured and the ratio between the scyllo-inositol concentration or concentration-related signal or value and the myo-inositol concentration or concentration-related signal or value is determined.

6 Claims, 3 Drawing Sheets

MEANS AND METHODS FOR CLASSIFYING EGGS AS ORGANIC

RELATED APPLICATIONS

This application claims priority to European Application Serial No. 13151701.3 filed Jan. 17, 2013 which is expressly incorporated by reference herein in its entirety.

The invention relates to the fields of biology, analytical chemistry and stock breeding, in particular poultry breeding.

Eggs are consumed worldwide and have high nutritious value. They contain essential amino acids, minerals and important vitamins like vitamin B12 and vitamin A. Although different kinds of eggs are edible for humans, such as duck eggs and turtle eggs, chicken eggs are by far the most consumed.

In the last century, hens were often housed in cages in view of costs and efficacy considerations. However, there is an increasing demand by the public for more animal friendly and healthy products, so that different types of hen housing systems are nowadays applied.

There are 4 types of farming methods, but in fact there are two different systems: cages and aviaries.

The farming methods can be divided in:
0=organic eggs
1=free range eggs
2=barn eggs
3=eggs from caged hens In free range eggs systems, aviary systems, hens are kept in much bigger groups of 3.000 to 6.000 birds. They are free to move throughout the whole systems. The living space per bird is 1111 $cm^2$ in barn and 1666 $cm^2$ in free range and organic housing systems. The hens must have access to litter area (⅓ of floor). The eggs are laid in nests, where the eggs roll away on a belt. There are standards for feed trough length, number of drinking nipples, perch length and number of laying nests. Also daylight in the house is obligatory.

The differences between barn and free range are the access to a winter garden and an outer area of 4 $m^2$ per bird.

The differences between free range and organic are the lower density in the latter and the organic feed. Also the hens are not de-beaked in the organic system.

The main advantage of the barn and free range systems is the opportunity for the hens to behave more naturally, like laying eggs in a nest, dust bathing and going outside (Free range and organic).

The farming methods are legally described in EU-legislation and also in national quality control systems, like IKB guidelines as IKB-Ei in The Netherlands and KAT in Germany. The rules laid down in these national quality control systems do not belong to the legislation. They are not legal rules.

The figure 0, 1, 2 or 3 should be printed on each egg at the production farm. The basis for this is Regulation (EC) No 589/2008 on rules for implementing marketing standards The minimum requirements for systems of production for the various egg farming methods are as follows:

Organic Eggs

Organic eggs are produced by hens that have access to the outdoors and are fed organic feed. Basis animal welfare standards must be met, antibiotics are not allowed except during disease outbreaks, and forced molting by withholding food and water is not allowed.

Free Range Eggs

'Free-range eggs' must be produced in systems of production which satisfy at least the conditions specified in Article 4 of Council Directive 1999/74/EC.

In particular, the following conditions must be satisfied:

(a) hens must have continuous daytime access to open-air runs. However, this requirement does not prevent a producer from restricting access for a limited period of time in the morning hours in accordance with usual good farming practice, including good animal husbandry practice. In case of other restrictions, including veterinary restrictions, adopted under Community law to protect public and animal health, having the effect of restricting access of hens to open-air runs, eggs may continue to be marketed as 'free-range eggs' for the duration of the restriction, but under no circumstances for more than 12 weeks;

(b) open-air runs to which hens have access must be mainly covered with vegetation and not be used for other purposes except for orchards, woodland and livestock grazing if the latter is authorised by the competent authorities;

(c) the maximum stocking density of open-air runs must not be greater than 2 500 hens per hectare of ground available to the hens or one hen per 4 m2 at all times. However, where at least 10 m2 per hen is available and where rotation is practised and hens are given even access to the whole area over the flock's life, each paddock used must at any time assure at least 2.5 m2 per hen;

(d) open-air runs must not extend beyond a radius of 150 m from the nearest pophole of the building. However, an extension of up to 350 m from the nearest pophole of the building is permissible provided that a sufficient number of shelters as referred to in Article 4(1)(3)(b)(ii) of Directive 1999/74/EC are evenly distributed throughout the whole open-air run with at least four shelters per hectare.

Barn Eggs

'Barn eggs' must be produced in systems of production which satisfy at least the conditions specified in Article 4 of Directive 1999/74/EC.

Eggs from Caged Hens

In cage system a small group of hens is kept in a cage. In traditional cages the group size is 5 birds. There is a feed trough in front of the cage and two water nipples at the back. The eggs are laid on the cage floor and roll on a belt in front of the cage. The manure will fall through the cage floor on a manure belt.

The advantages of cage systems regarding the others systems are the lower cost price (lower feed intake and lower labor costs) and less vulnerable to diseases (no contact with manure)

'Eggs from caged hens' must be produced in systems of production which satisfy at least:

(a) the conditions specified in Article 5 of Directive 1999/74/EC until 31 Dec. 2011, the so called Traditional cages; or (b) the conditions specified in Article 6 of Directive 1999/74/EC, the Enriched cages. Basis: Directive 1999/74/EC on standards for protection laying hens Traditional Cages Until 31 Dec. 2011 cage systems had to comply at least with the following requirements:

1. at least 550 cm2 per hen of cage area, measured in a horizontal plane, which may be used without restriction, in particular not including non-waste deflection plates liable to restrict the area available, must be provided for each laying hen;

2. a feed trough which may be used without restriction must be provided. Its length must be at least 10 cm multiplied by the number of hens in the cage;

3. unless nipple drinkers or drinking cups are provided, each cage must have a continuous drinking channel of the same length as the feed trough mentioned in point 2. Where drinking points are plumbed in, at least two nipple drinkers or two cups must be within reach of each cage;
4. cages must be at least 40 cm high over at least 65% of the cage area and not less than 35 cm at any point;
5. floors of cages must be constructed so as to support adequately each of the forward-facing claws of each foot. Floor slope must not exceed 14% or 8%. In the case of floors using other than rectangular wire mesh, Member States may permit steeper slopes;
6. cages shall be fitted with suitable claw-shortening devices.

Rearing in these cages is prohibited with effect from 1 Jan. 2012. From 1 Jan. 2003 this kind of cases may not be built or brought into service for the first time.

In 2012 the Traditional cages had to be enriched due to EU welfare legislation (Regulation (EC) No 589/2008 on rules for implementing marketing standards). This means bigger cages for a larger group of hens (20-40) and more space per bird (750 $cm^2$ instead of 550 $cm^2$). At the same time the hen must have access to a laying nest and a perch (stick to rest on).

Laying hens must have:
(a) at least 750 cm2 of cage area per hen, 600 cm2 of which shall be usable; the height of the cage other than that above the usable area shall be at least 20 cm at every point and no cage shall have a total area that is less than 2000 cm2;
(b) a nest;
(c) litter such that pecking and scratching are possible;
(d) appropriate perches allowing at least 15 cm per hen;
2. a feed trough which may be used without restriction must be provided. Its length must be at least 12 cm multiplied by the number of hens in the cage;
3. each cage must have a drinking system appropriate to the size of the group; where nipple drinkers are provided, at least two nipple drinkers or two cups must be within the reach of each hen;
4. to facilitate inspection, installation and depopulation of hens there must be a minimum aisle width of 90 cm between tiers of cages and a space of at least 35 cm must be allowed between the floor of the building and the bottom tier of cages;
5. cages must be fitted with suitable claw-shortening devices.

The International Federation of Organic Agriculture Movements (IFOAM), the Food and Agriculture Organization (FAO), the World Health Organization (WHO) and the European Union have set standards for biological housing. For instance, European Council Directive 1999/74/EC, Regulation (EC) No. 1804/1999 and regulation (EC) No. 834/2007 outline minimum standards for housing systems and organic production methods. Furthermore, farmers are obliged to code their eggs, so that the house keeping systems are known to retailers and consumers. This obligation is regulated in Commission Directive 2002/4//EC of 30 Jan. 2002 on the registration of establishments keeping laying hens, covered by Council Directive 1999/74/EC (OJ 2002 L 30/44). As outlined above, in Europe, four types of eggs are currently available which are coded as follows:

| Egg type | Printed egg code |
| --- | --- |
| Organic | 0 |
| Free-range | 1 |
| Barn | 2 |
| Cage | 3 |

Typically, the production costs for the different kinds of eggs increase with decreasing egg code number: costs cage eggs<costs barn eggs<costs free-range eggs<costs biologic eggs. Particularly, in view of the relatively high production costs of organic eggs as compared to the other kinds of eggs, a significantly higher price is charged to consumers. This makes organic products susceptible to fraud, since the profit margins would raise if eggs produced by housing systems 1, 2 or 3 were sold as organic eggs (type 0). Likewise, in view of the relatively low production costs for cage eggs (type 3), the profit margins would also raise if cage eggs were sold as other types of eggs (2, 1 or 0). Therefore, controls are desired, in order to preserve the consumers' confidence. Currently, carotenoid profiling is used as a tool for authentication of organic eggs. Van Ruth et al. (Food Chemistry 126 (2011), 1299-1305) found a significantly higher concentration of luthein/zeaxanthin and a significantly lower concentration of canthaxanthin and two other, unknown, carotenoids in yolk of organic eggs as compared to other kinds of eggs. However, the carotenoid content in egg yolk is influenced by the carotenoid content of food that is provided to the hens, so that it is well possible to influence the yolk carotenoid content of eggs. Moreover, Freilander eggs naturally have a low carotenoid content. Cage Freilander eggs could therefore be erroneously classified as organic eggs.

Krawczyk et al (Arch. Geflügelk. 75(3) (2011), S. 151-157) studied the differences in cholesterol, vitamin and fatty acid content of yolk of cage eggs and free range eggs. Differences in yolk cholesterol, vitamin A and fatty acid concentrations between cage eggs and free range eggs were found. These differences are, however, also easily influenced by the diets of the hens so that cage eggs could be easily misclassified.

In view of the above, there is a need for additional analytical strategies for classifying eggs.

It is an object of the present invention to provide additional tools for classifying the housing systems of eggs.

Accordingly, the present invention provides a use of scyllo-inositol and/or *Staphylococcus* sp. as a marker for classifying the housing system of an egg or an egg pool.

The present inventors have surprisingly found that the concentration of scyllo-inositol in the yolk of organic eggs is significantly higher as compared to the yolk scyllo-inositol concentrations of caged eggs, barn eggs and free range eggs. Moreover, the present inventors have found that the concentration of *Staphylococcus* sp. is significantly lower on the egg shell of cage eggs as compared to barn eggs, free range eggs and organic eggs. Hence, interestingly, the extent of human intervention on hen housing can now be accurately measured. Now that this insight has been provided, it can be established whether or not a given egg, or a given egg pool, belongs to the class of organic eggs or barn eggs, by determining the scyllo-inositol and/or *Staphylococcus* sp. concentration. For instance, scyllo-inositol quantitation means are used for establishing the yolk scyllo-inositol concentration, and/or *Staphylococcus* sp. quantitation means are used for determining the egg shell *Staphylococcus* sp.

concentration. As outlined in more detail below, depending on the yolk scyllo-inositol concentration, an egg is classified as being either organic or non-organic. Alternatively, or additionally, depending on the egg shell *Staphylococcus* sp. concentration an egg is classified as being either a cage egg or a non-cage egg. This allows for control of egg classification anywhere within the production chain, which reduces the chances of fraud and, therefore, will increase customer confidence.

Scyllo-inositol is one of the stereo-isomers of inositol (CAS 488-59-5). Synonyms of scyllo-inositol are scyllitol, cocositol and 1,3,5/2,4,6-hexahydroxycyclohexane. Its IUPAC name is (1R,2R,3R,4R,5R,6R)-Cyclohexane-1,2,3,4,5,6-hexanol and it is represented by the following Formula:

Formula 1

Scyllo-inositol

The present inventors have found that the concentrations of (free or non-phosphorylated) scyllo-inositol in egg yolk from organic eggs is significantly higher than in egg yolk of other kinds of eggs. The invention therefore provides a use of at least one scyllo-inositol quantitation means for determining whether an egg, or an egg pool, belongs to the class of organic eggs. In particular, it has been found that the average scyllo-inositol concentration in egg yolk of organic eggs is higher than 4.1 µg/ml yolk, whereas the average scyllo-inositol concentration in egg yolk of non-organic eggs is lower than 4.1 µg/ml yolk. Provided is therefore a method for determining whether an egg, or an egg pool, belongs to the class of organic eggs, the method comprising:

measuring the yolk scyllo-inositol concentration of said egg, or the yolk scyllo-inositol concentration of at least one egg from said egg pool; and classifying said egg or egg pool as belonging to the class of organic eggs when said scyllo-inositol concentration is higher than 4.1 µg/ml. Preferably, it is determined whether said yolk scyllo-inositol concentration is higher than 4.5 µg/ml. In one embodiment, it is determined whether said yolk scyllo-inositol concentration is higher than 5.0 µg/ml, or even higher than 5.5 µg/ml. As shown in the Examples, these values are particularly indicative for organic eggs.

As used herein, an egg pool is defined as a multitude of eggs, preferably originating from the same farmer. Typically, in Europe eggs are transported in pellets of 10500 eggs. Such pellet is, therefore, a (non-limiting) example of an egg pool according to the present invention. Since the determination of the yolk content of scyllo-inositol involves the destruction of the egg, one or a few eggs are typically used as random samples for classifying the other eggs of an egg pool. In one preferred embodiment, 3-10 eggs are tested per pellet of 10500 eggs.

A scyllo-inositol concentration is measured using any analytical method known in the art.

For instance, Anion-Exchange Chromatography (AEC) is used. This technique, known in the art, separates anionic compounds or analytes that can be ionized at high pH values. In one embodiment, AEC with pulsed amperometric detection (AEC-PAD) or LCAEC-PAD is used. This involves the application of various potentials to a working electrode over a specific time period, resulting in oxidizing and reducing conditions on the electrode surface (typically Au). This way, analytes bound to the working electrode surface are oxidized, resulting in anions that are detected with AEC. When a positive potential is applied, carbohydrates are electrocatalytically oxidezed at the surface of the electrode at high pH. This generates a current, which is proportional to the concentration of the carbohydrate. Hence, the scyllo-inositol concentration can be quantified using AEC-PAD or LCAEC-PAD by measuring the current that arises at a positive potential. In one embodiment, LCAEC or AEC is performed in a miniaturized assay, for instance as a lab on a chip.

In another embodiment, gas chromatography-mass spectrometry (GC-MS after a derivatisation step) is used. This technique, also well known in the art, involves a gas chromatograph and a mass spectrometer. In the gas chromatograph, compounds are separated in a capillary column due to differences in, for instance, sizes and/or chemical properties. Each separated compound is subsequently ionized and detected by the mass spectrometer downstream of the GC column. In yet another embodiment, liquid chromatography-mass spectrometry (LC-MS) is used. This technique, which is also well known in the art, involves a liquid chromatograph and a mass spectrometer. Liquid compounds are separated from each other in a column, where after each separated compound is ionized and detected by the mass spectrometer downstream of the LC column.

Further examples of scyllo-inositol quantitation means are scyllo-inositol-specific antibodies and enzymes which have scyllo-inositol as a substrate. The scyllo-inositol concentration in egg yolk is for instance determined in binding assays using scyllo-inositol-specific antibodies, or in enzymatic reaction assays using enzymes which have scyllo-inositol as a substrate. The extent of binding or the progress of an enzymatic reaction is preferably quantified using a detectable label.

In one embodiment, the absolute scyllo-inositol concentration in egg yolk is determined (for instance using calibrators or internal or external references). Preferably, however, the relative scyllo-inositol concentration is measured, meaning that the yolk scyllo-inositol concentration relative to the concentration of another compound is determined. Such compound preferably has a low concentration variety. This provides the advantage that small variations in the reaction conditions of two separate measurements affect the outcomes of two different tests to a lesser extent. For instance, if a small difference in reaction conditions (such as, for instance, the temperature) results in a somewhat lower value of the measured concentration of scyllo-inositol, the measured concentration of the other compound will, in general, also be somewhat lower. In such case, the measured values of the absolute scyllo-inositol concentrations will vary between a first and a second test. However, if the ratio between the measured scyllo-inositol concentration and the measured concentration of the other compound is taken, the outcomes of the first and second tests will, in principle, be more identical. In conclusion, measuring the scyllo-inositol concentration relative to the concentration of another compound will result in a (relative concentration) value that will differ less between individual tests. One embodiment therefore provides a method according to the invention, wherein the ratio between the yolk scyllo-inositol concentration and the concentration of another compound is measured. Said other compound is preferably another egg yolk compound.

In a particularly preferred embodiment, the ratio between yolk scyllo-inositol and yolk myo-inositol (CAS 87-89-8) is measured. Myo-inositol ((1R,2R,3S,4S,5R,6S)-cyclohexane-1,2,3,4,5,6-hexol) is another stereo-isomer of inositol. It plays an important role as the structural basis for a number of various inositol phosphates in eukaryotic cells. In addition, inositol serves as an important component of the structural lipid phosphatidylinositol (PI) and the phosphatidylinositol phosphate (PIP) lipids. Myo-inositol is represented by the following Formula:

Formula 2

Myo-inositol

According to the present invention, the ratio between the yolk scyllo-inositol concentration and the yolk myo-inositol concentration provides information whether an egg is an organic egg or a non-organic egg. However, in practice, the actual concentrations of scyllo-inositol and myo-inositol do not need to be assessed, as long as signals or values that are related to the concentrations are obtained in an assay. For instance, when chromatography is used, a graph will be obtained with several peaks wherein each peak represents the amount of a certain compound. The height of the peaks, and the surface below the peaks, are proportional to the concentrations of the compounds. Hence, when a ratio between a scyllo-inositol concentration and a myo-inositol concentration is to be determined, it is also possible to calculate the ratio between the heights of the scyllo-inositol peak and the myo-inositol peak obtained in a chromatography assay. Likewise, the ratio between the surface below the scyllo-inositol peak and the surface below the myo-inositol peak obtained in a chromatography assay can be calculated. As used herein, a signal or value that is proportional to the concentration of a given compound is called "a concentration-related signal or value". Non-limiting examples of such concentration-related signals or values are the peak heights or surfaces below peaks in a chromatography graph.

According to the present invention, the ratio between the yolk scyllo-inositol concentration and the yolk myo-inositol concentration is higher than 0.05 in organic eggs, whereas the ratio between the yolk scyllo-inositol concentration and the yolk myo-inositol concentration is lower than 0.05 in non-organic eggs. Likewise, the ratio between a concentration-related signal or value of scyllo-inositol and a concentration-related signal or value of myo-inositol is higher than 0.05 when organic eggs are analyzed, whereas such ratio is lower than 0.05 when non-organic eggs are analyzed. Now that this insight has been provided, it has become possible to classify an egg, or a pool of eggs, by measuring the ratio between the yolk scyllo-inositol and myo-inositol concentrations, or concentration-related signals or values thereof. One embodiment therefore provides a method for determining whether an egg, or an egg pool, belongs to the class of organic eggs, the method comprising:

measuring the yolk scyllo-inositol and myo-inositol concentrations of said egg, or of at least one egg from said egg pool, or measuring yolk scyllo-inositol and myo-inositol concentration-related signals or values of said egg, or of at least one egg from said egg pool; and classifying said egg or egg pool as belonging to the class of organic eggs when the ratio between said scyllo-inositol concentration or concentration-related signal or value and said myo-inositol concentration or concentration-related signal or value is higher than 0.05.

Preferably, it is determined whether said ratio between said scyllo-inositol concentration or concentration-related signal or value and said myo-inositol concentration or concentration-related signal or value is higher than 0.06, even more preferably higher than 0.07, and most preferably higher than 0.08. As shown in the Examples, these values are particularly indicative for organic eggs.

One of the advantages of the methods according to the present invention is the fact that scyllo-inositol is not easily artificially increased in the yolk of non-organic eggs, because it is distributed over various food component(s). Hence, it is not easily possible to commit fraud by administering a certain scyllo-inositol enhancing food component to hens in a non-organic housing system. Moreover, scyllo-inositol itself is difficult to produce and, therefore, expensive. Therefore, administration of pure scyllo-inositol to non-organic hens in order to commit fraud is also not a commercial option.

Now that means and methods according to the present invention are provided, it has become possible to prepare a kit of parts that is dedicated to classifying eggs using scyllo-inositol quantitation means. One embodiment therefore provides a kit of parts, comprising at least one scyllo-inositol quantitation means and at least one egg holder or a holder for egg yolk. Another embodiment provides a kit of parts, comprising at least one scyllo-inositol quantitation means and instructions for using these scyllo-inositol quantitation means for determining whether an egg, or an egg pool, belongs to the class of organic eggs. As described before, typical examples of suitable scyllo-inositol quantitation means are ion chromatographic means, preferably on chip (LOC). A kit of parts comprising a lab on a chip with scyllo-inositol quantitation means and at least one egg holder or holder for egg yolk is therefore also provided, as well as a kit of parts comprising a lab on a chip with scyllo-inositol quantitation means and instructions for using these scyllo-inositol quantitation means for determining whether an egg, or an egg pool, belongs to the class of organic eggs. In another embodiment, a kit of part according to the invention comprises at least one scyllo-inositol-specific antibody or at least one enzyme that has scyllo-inositol as a substrate.

The invention also provides means and methods for determining whether an egg, or an egg pool, belongs to the class of cage eggs. The present invention provides the insight that the amount of Staphylococcus species on the shell of cage eggs is significantly lower as compared to non-cage eggs such as barn eggs, free range eggs or organic eggs. Further provided is therefore a use of at least one Staphylococcus sp. quantitation means for determining whether an egg, or an egg pool, belongs to the class of cage eggs. The invention also provides a method for determining whether an egg, or an egg pool, belongs to the class of cage eggs, the method comprising:

measuring the egg shell *Staphylococcus* sp. concentration of said egg, or the egg shell *Staphylococcus* sp. concentration of at least one egg from said egg pool;

optionally, comparing said *Staphylococcus* sp. concentration with at least one reference value; and classifying said egg or egg pool as belonging to the class of cage eggs when said *Staphylococcus* sp. concentration is indicative for cage eggs, or classifying said egg or egg pool as belonging to the class of non-cage eggs when said *Staphylococcus* sp. concentration is indicative for non-cage eggs. Said reference value preferably comprises a cage egg-specific threshold value. Also provided is therefore a method for determining whether an egg, or an egg pool, belongs to the class of cage eggs, the method comprising:

measuring the egg shell *Staphylococcus* sp. concentration of said egg, or the egg shell *Staphylococcus* sp. concentration of at least one egg from said egg pool; and classifying said egg or egg pool as belonging to the class of cage eggs when said *Staphylococcus* sp. concentration does not exceed a cage egg-specific threshold value. Such threshold value is determined using any method well known in the art. In one embodiment, the *Staphylococcus* sp. nucleic acid concentration is measured on the egg shells of a plurality of cage eggs, and an average value is calculated ("cage egg average amount"). Additionally, the *Staphylococcus* sp. nucleic acid concentration is measured on the egg shells of a plurality of non-cage eggs, and an average value is calculated ("non-cage egg average amount"). Subsequently, a comparison between the cage egg average amount and the non-cage egg average amount yields a cage egg-specific threshold value. This cage egg-specific threshold value preferably lies between the cage egg average amount and the non-cage egg average amount and is chosen such that the *Staphylococcus* sp. concentrations of a statistically relevant amount of cage eggs are lower than the cage egg-specific threshold value and the *Staphylococcus* sp. concentrations of a statistically relevant amount of non-cage eggs are higher than the cage egg-specific threshold value. Hence, the measured egg shell *Staphylococcus* sp. concentration is compared with at least one reference value in order to classify the egg or egg pool. A reference can be a *Staphylococcus* sp. concentration, or a range of *Staphylococcus* sp. concentrations, that is present on the shell of cage eggs. Alternatively, or additionally, a reference can be a *Staphylococcus* sp. concentration, or a range of *Staphylococcus* sp. concentrations, that is present on the shell of non-cage eggs. In one embodiment, a reference value that lies between the cage egg-specific *Staphylococcus* sp. concentration(s) and the non-cage egg-specific *Staphylococcus* sp. concentration(s) is chosen. Subsequently, a measured *Staphylococcus* sp. concentration value is compared with any of said references. If the measured value is close to said reference cage egg-specific *Staphylococcus* sp. concentration, or within said reference range of cage egg-specific *Staphylococcus* sp. concentrations, the egg or pool of eggs is classified as a cage egg. If the measured value is significantly different from said reference cage egg-specific *Staphylococcus* sp. concentration, or outside said reference range of cage egg-specific *Staphylococcus* sp. concentrations, the egg or pool of eggs is classified as a non-cage egg. A similar comparison can be made between a measured value and a reference non-cage egg-specific *Staphylococcus* sp. concentration, or a reference range of non-cage egg-specific *Staphylococcus* sp. concentrations.

Various methods are known in the art for quantifying bacterial organisms such as *Staphylococcus* sp. Preferably, bacterial nucleic acid is amplified in an amplification reaction such as for instance (but not limited to) PCR and quantified using, for instance, fluorescent dyes or labeled probes. In a preferred embodiment, a real-time amplification reaction is performed. Nucleic acid is quantified using probes with a label that become detectable after the probe has been used in the amplification reaction (for instance, a fluorescent reporter probe, containing a fluorescent moiety that is quenched by a quencher and only becomes visible after the probe is degraded by Taq polymerase). In such real time amplification assay, fluorescence is plotted against the number of cycles on a logarithmic scale. The number of cycles at which a fluorescence is obtained that exceeds the background threshold (the cycle threshold (Ct) value) is indicative for the original amount of nucleic acid. In a preferred embodiment, real time PCR is used for quantifying *Staphylococcus* sp. nucleic acid. According to the present invention, an egg is classified as a cage egg when the $C_t$ value in a PCR analysis is higher than 2.6. If the $C_t$ value is lower, the egg is classified as a non-cage egg.

To quantify gene expression, the $C_q$ for a *Staphylococcus* nucleic acid sequence is preferably divided by the $C_q$ of the total bacterial nucleic acid of the egg shell sample to normalize for variation in the reaction conditions and the variation in nucleic acid amount between different samples. This normalization procedure permits comparison of the amount of *Staphylococcus* nucleic acid among different samples. According to the invention, an egg is classified as a cage egg when the ratio between the $C_t$ value for the *Staphylococcus* nucleic acid and the total bacterial nucleic acid is higher than 1.08.

Further provided is therefore a method for determining whether an egg, or an egg pool, belongs to the class of cage eggs, the method comprising:

amplifying egg shell *Staphylococcus* sp. nucleic acid of said egg, or egg shell *Staphylococcus* sp. nucleic acid of at least one egg from said egg pool, using a real time amplification method; and classifying said egg or egg pool as belonging to the class of cage eggs when the *Staphylococcus* sp. $C_t$ (cycle threshold) value is higher than 2.6 or the ratio between the $C_t$ value for the *Staphylococcus* nucleic acid and the total bacterial nucleic acid is higher than 1.08. Said real time amplification method is preferably real time PCR (qPCR).

Now that means and methods according to the present invention are provided, it has become possible to prepare a kit of parts that is dedicated to classifying eggs using *Staphylococcus* sp. quantitation means. One embodiment therefore provides a kit of parts, comprising at least one *Staphylococcus* sp. quantitation means and means for obtaining bacterial nucleic acid from egg shells. Such means for instance comprises a swab. Another embodiment provides a kit of parts, comprising at least one *Staphylococcus* sp. quantitation means and instructions for using these *Staphylococcus* sp. quantitation means for determining whether an egg, or an egg pool, belongs to the class of cage eggs. Typical (non-limiting) examples of such *Staphylococcus* sp. quantitation means include at least one *Staphylococcus*-specific primer and/or a *Staphylococcus*-specific probe, preferably a *Staphylococcus*-specific fluorescent reporter probe.

The invention is further explained in the following examples. These examples do not limit the scope of the invention, but merely serve to clarify the invention.

EXAMPLES

Example 1

Results&Methods

In order to find markers for the different categories of eggs, GC-MS was used to analyse samples from 1800 eggs from 60 farms. The 1800 eggs were pooled per ten, resulting in three pools for each farm. The GC-MS method used involved oximation and sylilation as derivatisation steps and has been described before in the literature [Microbial Metabolomics with Gas Chromatography/Mass Spectrometry, Maud M. Koek, Bas Muilwijk, Maria J. van der Werf, and Thomas Hankemeier, Analytical Chemistry, 2006, 78 (4), pp 1272-128].

Figure 1:
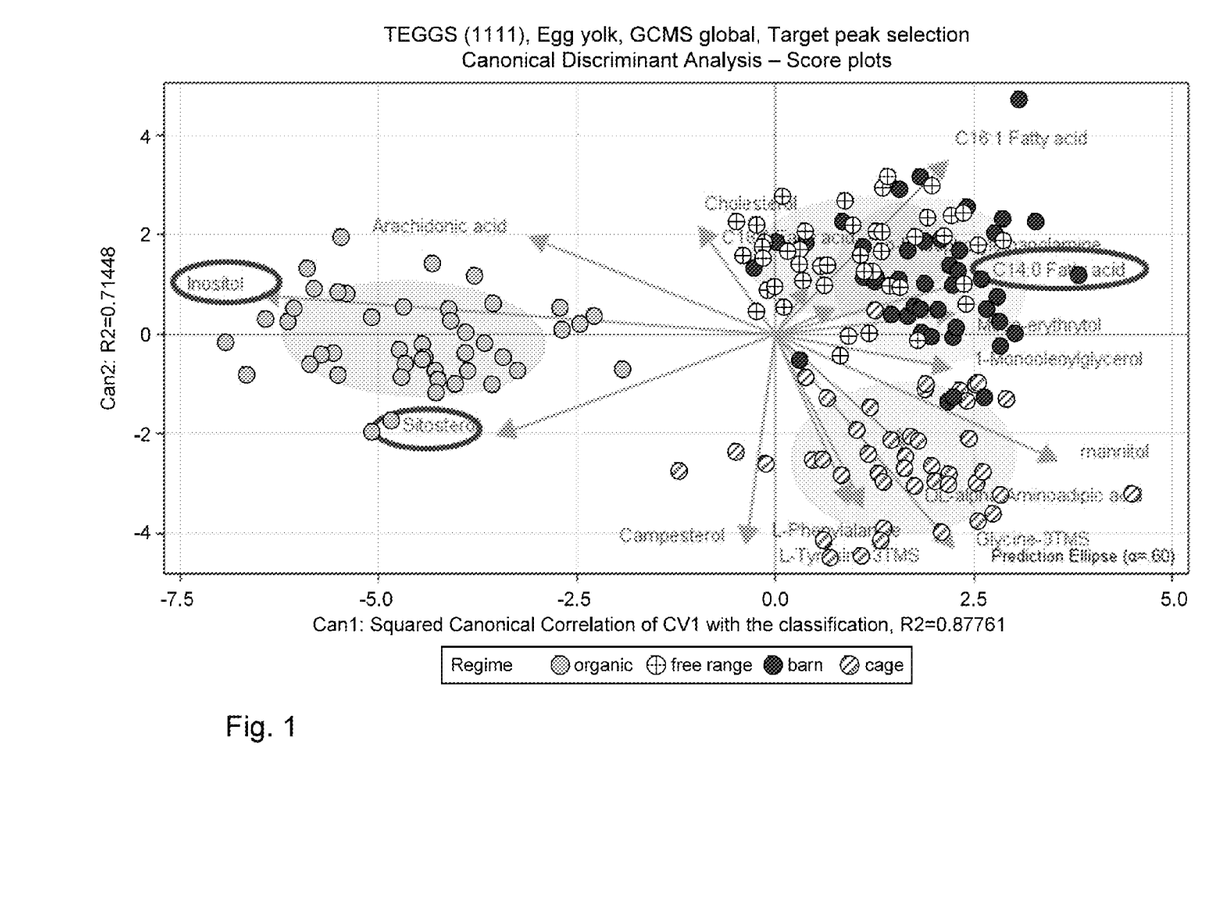
FIG. 1 shows canonical discriminant analysis GC-MS data.

The data was analysed with multivariate statistical method Canonical Discriminant Analysis (a dimension-reduction technique related to principal component analysis and canonical correlation). With this method scyllo-inositol was identified as a potential marker compound (see FIG. 1).

Study 1111, BQ 1, RQ101-[all_poiint(allpointslvl), no_time(notime)], Last data update 16 Aug. 2010 03:44:33 (180 samples, 16 peaks). Canonical Discriminant Analysis, Method=Normal(parametric), Discriminant functions=Linear, Distances=Pooled covariance matrix, 3 canonical variables, the data are autoscaled TNO AR DWH Development Version 0.9 (SAS V9.2) Monday 16 Aug. 2010. 06:40/Generated by kistermalk erc.

In order to quantify the scyllo-inositol marker, IC-PAD was performed in two different assays.
Assay 1) Including validation marker with GC-MS data, 1200 eggs (40 farms), pools of 3 eggs (see FIG. 2).
Assay 2), 120 eggs (12 farms), pools of 3 eggs (see FIG. 3).

TABLE 1

| | Conc. Scyllo-inositol (mg/ml) in egg yolk | | | | Ratio scyllo/myo-inositol in egg yolk | | | |
|---|---|---|---|---|---|---|---|---|
| | Av bio | Stdev bio | Av other | Stdev other | Av bio | Stdev bio | Av other | Stdev other |
| First series | 5.70 | 0.84 | 2.11 | 0.75 | 0.062 | 0.01 | 0.022 | 0.01 |
| Second series | 5.91 | 0.98 | 2.71 | 0.88 | 0.046 | 0.005 | 0.024 | 0.007 |

Figure 2:
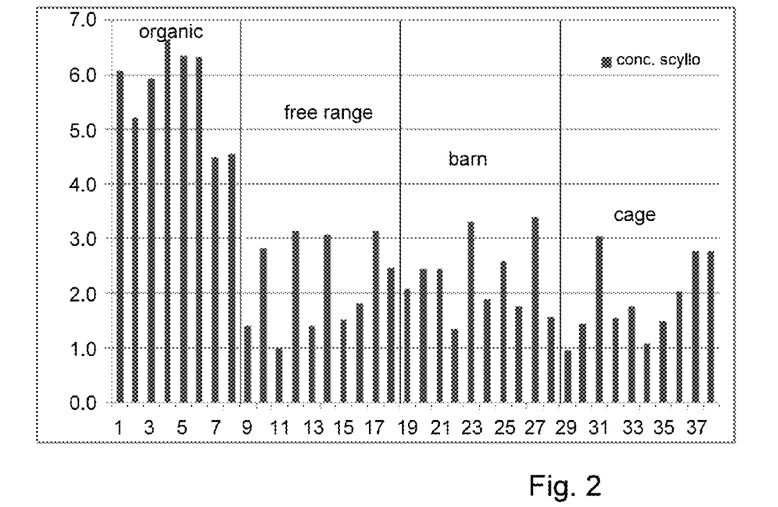
FIG. 2 shows scyllo-inositol in first assay.
Figure 3:
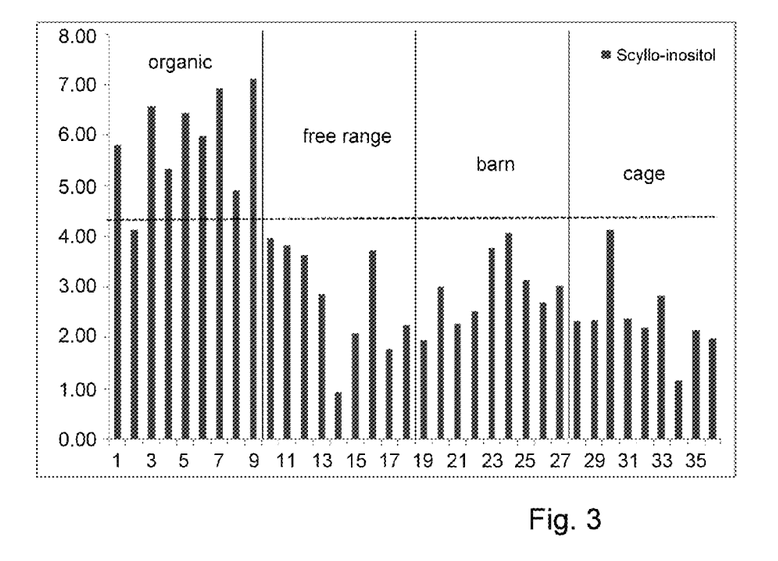
FIG. 3 shows scyllo-inositol in second assay.

Importantly, it is shown in FIGS. 2 and 3 that the yolk scyllo-inositol concentrations of organic eggs and non-organic eggs do not overlap. This means that determination of yolk scyllo-inositol concentration is a reliable test with a very low chance of false-positive results (meaning that the chance that a non-organic egg is erroneously classified as an organic egg is very small).

Example 2

Figure 4:
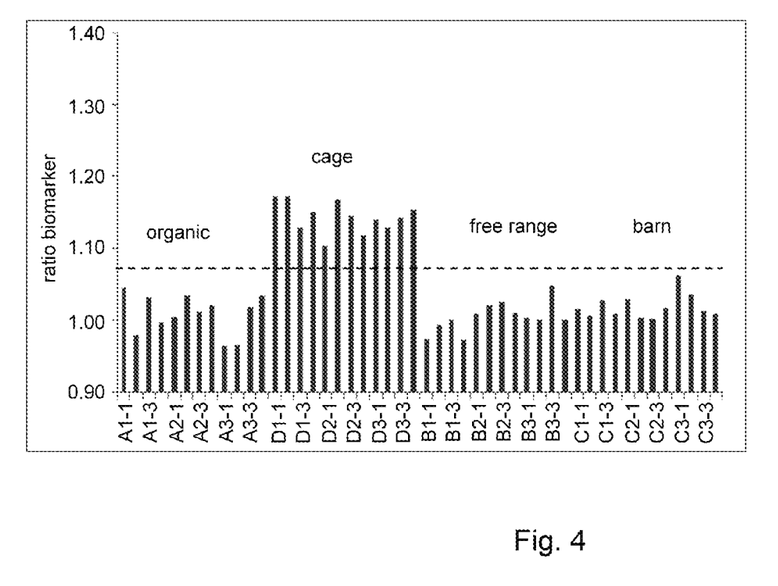
FIG. 4 shows results of qPCR analysis *Staphylococcus* sp. (Example 2).

A flora analysis was carried out in order to search for additional markers. For each category, (cage, barn, free range and organic) 12 eggs were used. From this analysis it was concluded that *Staphylococcus* sp. could be used as a marker for cage eggs. Subsequently, a qPCR was performed in order to quantify the *Staphylococcus* nucleic acid amount on the shells of cage, barn, free range and organic eggs. The results are shown in Table 2 and FIG. 4.

TABLE 2

| | av $C_t$ marker | stdev CT marker | av Ct total DNA | av ratio (Ct, m/Ct, tot) | stdev (Ct, m/Ct, tot) |
|---|---|---|---|---|---|
| Cage | 29.510 | 1.971 | 25.806 | 1.144 | 0.022 |
| Barn | 22.142 | | 21.745 | 1.019 | 0.018 |
| Free range | 21.331 | | 21.235 | 1.005 | 0.021 |
| Organic | 24.205 | | 23.995 | 1.009 | 0.028 |

It is concluded that cage eggs can be distinguished from the other egg categories (barn, free range and organic). An egg is classified as a cage egg when the $C_t$ value is higher than 2.6. If the $C_t$ value is lower, the egg is classified as a non-cage egg. Moreover, an egg is classified as a cage egg when the ratio between the $C_t$ value for the *Staphylococcus* nucleic acid and the total bacterial nucleic acid is higher than 1.08. If this ratio is 1.02 or lower, the egg is classified as a non-cage egg.

REFERENCES

Maud M. Koek, Bas Muilwijk, Maria J. van der Werf, and Thomas Hankemeier. Microbial Metabolomics with Gas Chromatography/Mass Spectrometry. Analytical Chemistry, 2006, 78 (4), pp 1272-128

Krawczyk et al. Effect of housing system on cholesterol, vitamin and fatty acid content of yolk and physical characteristics of eggs from Polish native hens. Arch. Geflügelk. 75(3) (2011), S. 151-157

Van Ruth et al. Authentication of organic and conventional eggs by carotenoid profiling. Food Chemistry 126 (2011), 1299-1305

The invention claimed is:

1. A method for separating caged chicken eggs, barn chicken eggs, and free range chicken eggs from organic chicken eggs, the method comprising:
   a) measuring yolk scyllo-inositol and yolk myo-inositol concentrations of a chicken egg from an egg pool, or yolk scyllo-inositol and yolk myo-inositol concentration-related signals or values of a chicken egg from an egg pool;
   b) calculating a ratio between said scyllo-inositol concentration or concentration-related signal or value and said myo-inositol concentration or concentration-related signal or value; and
   c) physically coding the egg pool as an organic egg pool if the ratio is at least 0.046, or coding the egg pool as a free range, barn, or caged egg pool if the ratio is less than 0.046 where coding makes the class of the eggs known to retailers and consumers.

2. The method according to claim 1, wherein said scyllo-inositol and/or myo-inositol concentrations or concentration-related signals or values are measured using Anion-Exchange Chromatography (AEC), liquid chromatography anion exchange chromatography (LCAEC), AEC with pulsed amperometric detection (AEC-PAD), LCAEC-PAD, gas chromatography-mass spectrometry (GC-MS), and/or liquid chromatography-mass spectrometry (LC-MS).

3. The method of claim 1, wherein said yolk scyllo-inositol and/or yolk myo-inositol concentrations or concentration-related signals or values are measured using a lab on a chip.

4. The method of claim 1 where physically coding is printing a code on the eggs.

5. A method for separating caged chicken eggs, barn chicken eggs, and free range chicken eggs from organic chicken eggs, the method comprising:
   a) measuring yolk scyllo-inositol and yolk myo-inositol concentrations of a chicken egg from an egg pool, or yolk scyllo-inositol and yolk myo-inositol concentration-related signals or values of a chicken egg from an egg pool;
   b) calculating a ratio between said scyllo-inositol concentration or concentration-related signal or value and said myo-inositol concentration or concentration-related signal or value;
   c) physically separating the egg pool as an organic egg pool if the ratio is at least 0.046, or physically separating as a free range, barn, or caged egg pool if the ratio is less than 0.046; and
   d) coding the egg pool as an organic egg pool if the ratio is at least 0.046, or coding as a free range, barn, or caged egg pool if the ratio is less than 0.046.

6. The method of claim 5 where coding prints a code on the eggs.

* * * * *